(12) United States Patent
Lin et al.

(10) Patent No.: US 6,780,843 B2
(45) Date of Patent: Aug. 24, 2004

(54) SEQUENCE AND METHOD FOR GENETIC ENGINEERING OF PROTEINS WITH CELL MEMBRANE TRANSLOCATING ACTIVITY

(75) Inventors: Yao-Zhong Lin, Nashville, TN (US); John P. Donahue, Nashville, TN (US); Mauricio Rojas, Nashville, TN (US); ZhongJia Tan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 310 days.

(21) Appl. No.: 10/116,288

(22) Filed: Apr. 4, 2002

(65) Prior Publication Data

US 2002/0143142 A1 Oct. 3, 2002

Related U.S. Application Data

(62) Division of application No. 09/562,868, filed on May 1, 2000, now Pat. No. 6,432,680, which is a division of application No. 09/186,170, filed on Nov. 4, 1998, now Pat. No. 6,248,558.
(60) Provisional application No. 60/080,083, filed on Mar. 31, 1998.

(51) Int. Cl.$^7$ .................. A61K 38/04; C07K 14/00
(52) U.S. Cl. .................. 514/2; 514/12; 514/14; 530/300; 530/327; 530/328; 435/69.7; 435/320.1; 435/252.3
(58) Field of Search ............... 514/2, 12, 14; 530/300, 327, 328; 435/252.3, 320.1, 69.7

(56) References Cited

PUBLICATIONS

Blattner et. al., H65071 (Gene Bank Accession No., Oct. 8, 1999).
Rojas et al. "Genetic Engineering of Proteins with Cell Membrane Permeability," *Nature Biotechnology*, 16:370–375 (1998).
*Pharmaceutical Research*, vol. 14, No. 12, 1997, "Cellular Delivery of Oligonucleotides by Synthetic Import Peptide Carrier" by Sujatha Dokka, David Toledo–Velasqez, Xianglin Shi, Liying Want, and Yon Rojanasakul.
*The Journal of Biological Chemistry*, vol. 269, No. 14, Issue of Apr. 8, 1994, pp. 10444–10450, "The Third Helix of the Antennapedia Homeodomain Translocates through Biological Membranes" by Daniele Derossi, Alain H. Joliot, Gerard Chassaing, and Alain Prochiantz.
*Journal of Peptide Research*, 51, 1998, 235–243, "Conformational and topological requirements of cell–permeable peptide function" by Caigan Du, Songyi Yao, Mauricio Rojas and Yao–Zhong Lin.
*The Journal of Biological Chemistry*, vol. 271, No. 10, Issue of Mar. 8, 1996, pp. 5305–5308, "Role of Nuclear Localization Sequence in Fibroblast Growth Factor–1–stimulated Mitogenic Pathways" by Yao–Zhong Lin, SongYi Yao, and Jacek Hawiger.
*The Journal of Biological Chemistry*, vol. 270, No. 24, Issue of Jun. 16, 1995, pp. 14255–14258, "Inhibition of Nuclear Translocation of Transcription Factor NF–κB by a Synthetic Peptide Containing a Cell Membrane–permeable Motif and Nuclear Localization Sequence" by Yao–Zhong Lin, SongYi Yao, Ruth Ann Veach, Troy R. Torgerson, and Jacek Hawiger.
*Gene*, (1988) 31–40, "Single–step purification of polypeptides expressed in *Escherichia coli* as fusions with glutathione S–transferase," by Donald B. Smith and Kevin S. Johnson.
*The Journal of Biological Chemistry*, vol. 271, No. 44, Issue of Nov. 1, 1996, pp. 27456–27461, "Controlling Epidermal Growth Factor (EGF)–stimulated Ras Activation in Intact Cells by a Cell–permeable Peptide Mimicking Phosphorylated EGF Receptor," by Mauricio Rojas, SongYi Yao, and Yao–Zhong Lin.

*Primary Examiner*—Christopher S. F. Low
*Assistant Examiner*—Chih-Min Kam
(74) *Attorney, Agent, or Firm*—Needle & Rosenberg, P.C.

(57) ABSTRACT

The invention describes a membrane-translocating peptide sequence (MTS) which facilitates entry of polypeptides and proteins into cells. Also described is an isolated nucleotide sequence encoding the membrane-translocating peptide and a method of using this sequence to genetically engineer proteins with cell membrane permeability. The MTS, and the method of genetically engineering proteins with cell membrane permeability, are useful for polypeptide and protein delivery for human and veterinary applications such as vaccine delivery and cancer therapy.

5 Claims, 9 Drawing Sheets

Protein (μM): 0 3 10 20

Total cell lysate
blot Ab: αGST

Incubation
temperature: 4°C 22°C 37°C

Total cell lysate
blot Ab: αGST

Incubation
time (hours): — 0.5 1 2 6 18

Total cell lysate
blot Ab: αGST

U.S. Pat. No. 6,780,843 B2

SEQUENCE LISTING

<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Amino acid
      sequence of peptide which transports proteins
      through the cell membrane into the cell.
<220> FEATURE:

```
<221> NAME/KEY: PEPTIDE
<222> LOCATION: (1)..(12)
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 1

Ala Ala Val Leu Leu Pro Val Leu Leu Ala Ala Pro
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:  Amino acid
      sequence of peptide which transports proteins
      through the cell membrane into the cell.
<220> FEATURE:
<221> NAME/KEY: PEPTIDE
<222> LOCATION: (1)..(8)
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 2

Ala Ala Val Leu Leu Pro Val Leu
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Amino acid
      sequence of peptide which transports proteins
      through the cell membrane into the cell.
<220> FEATURE:
<221> NAME/KEY: PEPTIDE
<222> LOCATION: (1)..(9)
<300> PUBLICATION INFORMATION:
<301> AUTHORS: Rojas, M. et al.
<302> TITLE: "Genetic Engineering of Proteins with Cell Membrane
<302> TITLE: Permeability"
<303> JOURNAL: Nature Biotechnology
<304> VOLUME: 16
<305> ISSUE: April
<306> PAGES: 370-375
<307> DATE: 1998-04-01

<400> SEQUENCE: 3

Ala Ala Val Leu Leu Pro Val Leu Leu
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:  Amino acid
      sequence of peptide which transports proteins
```

```
        through the cell membrane into the cell.
<220> FEATURE:
<221> NAME/KEY: PEPTIDE
<222> LOCATION: (1)..(10)
<300> PUBLICATION INFORMATION:
<301> AUTHORS: Rojas, M. et al.
<302> TITLE: "Genetic Engineering of Proteins with Cell Membrane
        Permeability"
<303> JOURNAL: Nature Biotechnology
<304> VOLUME: 16
<305> ISSUE: April
<306> PAGES: 370-375
<307> DATE: 1998-04-01

<400> SEQUENCE: 4

Ala Ala Val Leu Leu Pro Val Leu Leu Ala
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence:  Amino acid
        sequence of peptide which transports proteins
        through the cell membrane into the cell.
<220> FEATURE:
<221> NAME/KEY: PEPTIDE
<222> LOCATION: (1)..(11)
<300> PUBLICATION INFORMATION:
<301> AUTHORS: Rojas, M. et al.
<302> TITLE: "Genetic Engineering of Proteins with Cell Membrane
        Permeability"
<303> JOURNAL: Nature Biotechnology
<304> VOLUME: 16
<305> ISSUE: April
<306> PAGES: 370-375
<307> DATE: 1998-04-01

<400> SEQUENCE: 5

Ala Ala Val Leu Leu Pro Val Leu Leu Ala Ala
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence : Amino acid
        sequence of peptide which transports proteins
        through cell membrane into the cell.
<220> FEATURE:
<221> NAME/KEY: PEPTIDE
<222> LOCATION: (1)..(8)
<300> PUBLICATION INFORMATION:
<301> AUTHORS: Rojas, M. et al.
<302> TITLE: "Genetic Engineering of Proteins with Cell Membrane
        Permeability"
<303> JOURNAL: Nature Biotechnology
<304> VOLUME: 16
<305> ISSUE: April
<306> PAGES: 370-375
<307> DATE: 1998-04-01

<400> SEQUENCE: 6

Leu Pro Val Leu Leu Ala Ala Pro
 1               5

<210> SEQ ID NO 7
<211> LENGTH: 9
<212> TYPE: PRT
<213> ORGANISM: Artificial Sequence
<220> FEATURE:
```

```
<223> OTHER INFORMATION: Description of Artificial Sequence: Amino acid
      sequence of peptide which transports proteins
      through the cell membrane into the cell.
<220> FEATURE:
<221> NAME/KEY: PEPTIDE
<222> LOCATION: (1)..(9)
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 7

Leu Leu Pro Val Leu Leu Ala Ala Pro
 1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Amino acid
      sequence of peptide which transports proteins
      through the cell membrane into the cell.
<220> FEATURE:
<221> NAME/KEY: PEPTIDE
<222> LOCATION: (1)..(10)
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 8

Val Leu Leu Pro Val Leu Leu Ala Ala Pro
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Amino acid
      sequence of peptide which transports proteins
      through the cell membrane into the cell.
<220> FEATURE:
<221> NAME/KEY: PEPTIDE
<222> LOCATION: (1)..(11)
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 9

Ala Val Leu Leu Pro Val Leu Leu Ala Ala Pro
 1               5                  10

<210> SEQ ID NO 10
<211> LENGTH: 36
<212> TYPE: DNA
```

```
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 10
gcagccgttc ttctccctgt tcttcttgcc gcaccc                                36

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 11
gcagccgttc ttctccctgt tctt                                             24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 12
gcagccgttc ttctccctgt tcttctt                                          27

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
```

```
<304> VOLUME: 16
<305> ISSUE: April
<306> PAGES: 370-375
<307> DATE: 1998-04-01

<400> SEQUENCE: 13
gcagccgttc ttctccctgt tcttcttgcc                                          30

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 14
gcagccgttc ttctccctgt tcttcttgcc gca                                      33

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 15
ctccctgttc ttcttgccgc accc                                                24

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 16
cttctccctg ttcttcttgc cgcaccc                                             27
```

```
<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 17
gttcttctcc ctgttcttct tgccgcaccc                                    30

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell
<300> PUBLICATION INFORMATION:
<301> AUTHORS: Rojas, M. et al.
<302> TITLE: "Genetic Engineering of Proteins with Cell Membrane
      Permeability"
<303> JOURNAL: Nature Biotechnology
<304> VOLUME: 16
<305> ISSUE: April
<306> PAGES: 370-375
<307> DATE: 1998-04-01

<400> SEQUENCE: 18
gccgttcttc tccctgttct tcttgccgca ccc                                33

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell

<400> SEQUENCE: 19
atcgaaggtc gtgggatcgc agccgttctt ctccctgttc ttcttgccgc acccgggatc   60
cccgggaatt catcgtga                                                 78

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence:  Amino acid
      sequence of peptide which transports proteins
      through the cell membrane into the cell.

<400> SEQUENCE: 20

Ile Glu Gly Arg Gly Ile Ala Ala Val Leu Leu Pro Val Leu Leu Ala
 1               5                  10                  15

Ala Pro Gly Ile Pro Gly Asn Ser Ser
            20                  25
```

```
<210> SEQ ID NO 21
<211> LENGTH: 77
<212> TYPE: DNA
<213> ORGANISM: Artificial Sequence
<220> FEATURE:
<223> OTHER INFORMATION: Description of Artificial Sequence:  Nucleotide
      sequence encoding peptide which transports
      proteins through the cell membrane into the cell.

<400> SEQUENCE: 21
atcgaaggtc gtgggatccc cgcagccgtt cttctccctg ttcttcttgc cgcaccctaa      60
gcgatccccg ggaattc                                                    77

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence:  Amino acid
      sequence of peptide which transports proteins
      through the cell membrane into the cell.

<400> SEQUENCE: 22

Ile Glu Gly Arg Gly Ile Pro Ala Ala Val Leu Leu Pro Val Leu Leu
 1               5                  10                  15

Ala Ala Pro

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence:  Amino acid
      sequence of peptide which transports proteins
      through the cell membrane into the cell.
<300> PUBLICATION INFORMATION:
<301> AUTHORS: Dokka, S.
<302> TITLE: "Cellular Delivery of Oligonucleotides by Synthetic Import
      Peptide Carrier"
<303> JOURNAL: Pharmaceutical Research
<304> VOLUME: 14
<305> ISSUE: 12
<306> PAGES: 1759 to 1764
<307> DATE: 1997-12

<400> SEQUENCE: 23

Ala Ala Val Ala Leu Leu Pro Ala Val Leu Leu Ala Leu Leu Ala Pro
 1               5                  10                  15
```

SEQUENCE AND METHOD FOR GENETIC ENGINEERING OF PROTEINS WITH CELL MEMBRANE TRANSLOCATING ACTIVITY

CROSS-REFERENCE TO RELATED APPLICATIONS

This application is a divisional of and claims benefit of priority from application U.S. Ser. No. 09/562,868, filed May 1, 2000, now U.S. Pat. No. 6,432,680, which is a divisional of and claims benefit of priority from application U.S. Ser. No. 09/186,170, filed Nov. 4, 1998, now U.S. Pat. No. 6,248,558, which claims benefit of priority from provisional application U.S. Serial No. 60/080,083 filed Mar. 31, 1998, all of which applications are herein incorporated by reference in their entireties.

STATEMENT OF FEDERALLY-SPONSORED RESEARCH

This invention was made with U.S. Governments support under grant GM52500, awarded by the National Institutes of Health. The U.S. Government has certain rights in this invention.

FIELD OF THE INVENTION

The present invention relates to: (1) DNA sequences encoding membrane-translocating peptide sequences; (2) sequences of membrane-translocating peptides; (3) fusion proteins endowing membrane-translocating potential upon biologically active polypeptides and proteins; and (4) expression vectors for production of said fusion proteins.

More specifically, the disclosed invention relates to a novel membrane-translocating sequence for directing import of biologically active protein molecules into a cell, and a method of using an expression vector in a host cell to produce a fusion protein comprising a membrane-translocating sequence and a biologically active polypeptide, protein domain, or protein.

BACKGROUND OF THE INVENTION

Signal peptide sequences mediate protein secretion and are composed of a positively charged amino terminus, a central hydrophobic core and a carboxyl-terminal cleavage site recognized by a signal peptidase. These sequences usually comprise 15 to 30 residues. Signal sequences used for targeting proteins to specific locations have been found in both prokaryotic and eukaryotic cells. In bacteria, phage fd signal sequences for the major and minor coat proteins direct those proteins to the inner membrane. The β-lactamase protein of pBR322 is directed to the periplasmic space by a different signal sequence, while outer membrane proteins such as OmpA are directed to their assigned destination by other signal sequences. Eukaryotic signal sequences directing translocation of the protein into the endoplasmic reticulum include that of human preproinsulin, bovine growth hormone, and the Drosophila glue protein. Near the N-terminus of such sequences are 2–3 polar residues, and within the signal sequence is a hydrophobic core consisting of hydrophobic amino acids. No other conservation of sequence has been observed (Lewin, 1994).

Peptide transport across the cell membrane has been demonstrated, for example, by a peptide representing the third helix of the Antennapedia homeodomain (Derossi et al., 1994). The transport peptide was not used to direct a cargo peptide through the cell membrane, however.

Biological membrane transport has been exploited for protein expression and export from transfected or transformed cells. Secretion of proteins, such as a globin protein, which would normally remain in the cytosol, has been achieved by adding a signal sequence to the N-terminus of the protein (Lewin 1994). Foreign genes have been inserted into recombinant DNA constructs for expression and secretion from bacterial cells, as described for example in U.S. Pat. No. 5,156,959, which discloses a method to export gene products into the growth medium of gram negative bacteria. U.S. Pat. No. 5,380,653 describes expression vectors and methods for intracellular protein production in Bacillus species. U.S. Pat. No. 5,712,114 describes a recombinant DNA construct for secretion of expressed proteins, particularly from *Hansenula polymorpha* cells, which utilizes the signal sequence of the human preprocollagen α-1 protein.

Lin et al. have described a method of using a naturally-occurring signal peptide sequence to import a cargo peptide into the cell (Lin et al., 1995). One signal sequence that has been successfully used for this cell-permeable peptide import is the 16-residue h region of the signal sequence of Kaposi fibroblast growth factor. The cargo peptide transported by this technique has thus far been limited to no more than 25 amino acids, however.

Until now, DNA constructs, including both DNA vaccines and recombinant viral constructs, have provided the most effective method for furnishing a protein product to the cell for processing and expression of antigenic determinants on the cell surface. The Food and Drug Administration has expressed concern about approval of DNA vaccines, however, citing animal studies in which anti-DNA antibodies have been formed. Recombinant viral vectors have posed a unique set of problems in terms of delivery into cells, efficiency of expression, and potential immune system response to viral proteins. Other methods of DNA transfer into cells, such as transfection and microinjection, are often inefficient and time-consuming.

Genetic disorders resulting from the production of defective protein products have been treated, with limited success, by gene therapy. No other method has shown as much promise for introducing a protein into the interior of a cell. Gene therapy, however, has proven to be more difficult than originally envisioned. Appropriate vectors are difficult to identify, expression is transient, and immune responses to some vectors, particularly viral vectors, may preclude repeated use. Delivery of the isolated protein for import into the affected cells would provide a more efficient and effective solution to the problem.

What is needed is a method for importing entire protein molecules into a cell for studies of intracellular processes in living systems, for drug delivery, for vaccine development, and for disease therapy.

SUMMARY OF THE INVENTION

The present invention relates to a novel and non-naturally occurring membrane-translocating sequence (MTS) which has been shown to mediate the transport of a full-length protein into a cell. As used herein, a membrane-translocating sequence is an amino acid sequence capable of mediating the import of a polypeptide, protein domain, or full-length protein through the cell membrane.

The invention further relates to a method of using such a membrane-translocating sequence to genetically engineer proteins with cell membrane permeability. An expression vector is designed so that the DNA sequence encoding the membrane-translocating peptide will be positioned N-terminal or C-terminal to the sequence encoding the target protein, in correct reading frame for expression of both MTS and a biologically-active target protein as a fusion product. Peptides, polypeptides, protein domains, or full-length proteins are expressed as a fusion product with the membrane-translocating sequence.

Expression vectors may be chosen from among those readily available for prokaryotic or eukaryotic expression systems.

Genetically engineered proteins prepared by the method of the present invention can be used as protein-based vaccines, particularly where killed or attenuated whole organism vaccines are impractical.

Cell-permeable proteins prepared by the method of the present invention can also be used for the treatment of disease, particularly cancer. Cell-permeable proteins can be delivered to the interior of the cell, eliminating the need to transfect or transform the cell with a recombinant vector.

Cell permeable polypeptides of the present invention can be used in vitro to investigate protein function, or can be used to maintain cells in a desired state.

The membrane translocating sequence (MTS) of the present invention can be used to deliver peptides, polypeptides, protein domains, or proteins to the interior of a target cell either in vitro or in vivo. The MTS can be linked to the target protein through a peptide linkage formed by expression of the fusion protein from a recombinant DNA or RNA molecule, or can be linked to the target protein by means of a linker covalently linked to the MTS. A covalent linkage can be used to link an MTS of the present invention to a non-protein molecule, such as a polynucleotide, for import into the cell.

BRIEF DESCRIPTION OF THE DRAWINGS

FIG. 3a illustrates indirect immunofluorescence microscopy of NIH 3T3 cells treated with GST-MTS1 fusion protein. FIG. 3b illustrates indirect immunofluorescence microscopy of NIH 3T3 cells treated with GST wild-type protein. FIG. 3c illustrates indirect immunofluorescence microscopy of untreated NIH 3T3 cells.

FIG. 6a illustrates concentration-dependence of the cellular import of GST-MTS1 protein. FIG. 6b illustrates temperature-dependence of the cellular import of GST-MTS1 protein. FIG. 6c illustrates time-dependence of the cellular import of GST-MTS1 protein. As shown in FIG. 6a, cells were treated with 0–20 μM concentrations of GST-MTS1 protein, as indicated. Total cell lysates were then analyzed by Western blot analysis using anti-GST antibody as probe. As shown in FIG. 6b, cells were treated with equal concentrations of GST-MTS1 protein at 4° C., 22° C., and 37° C., as indicated. Total cell lysates were then analyzed by Western blot with anti-GST antibody as probe. As shown in FIG. 6c, GST-MTS1 continued to accumulate intracellularly up to 18 hours of incubation, with only a small percentage of imported protein appearing degraded. Cells treated with 20 μM protein at 37° C. for the times indicated continued to import the protein.

FIG. 7a shows indirect immunofluorescence microscopy of serum-starved SAA cells treated with 2.5 μM GST-Grb2SH2-MTS. FIG. 7b shows indirect immunofluorescence microscopy of serum-starved SAA cells treated with 2.5 μM GST-Grb2SH2 protein for one hour, followed by treatment with epidermal growth factor (EGF) (50 ng/ml) for 10 minutes.

FIG. 8a illustrates Western blot analysis of cell lysates from SAA cells treated with the indicated proteins and EGF. FIG. 8b illustrates Western blot analysis of anti-Grb2 immunoprecipitates of cell lysates from SAA cells treated with GST-Grb2SH2-MTS at the indicated concentrations followed by EGF treatment (50 ng/ml) for 10 minutes. Probes were specific for phosphorylated EGF receptor (top panel) and Grb2 protein (bottom panel).

DETAILED DESCRIPTION OF THE INVENTION

Figure 1:
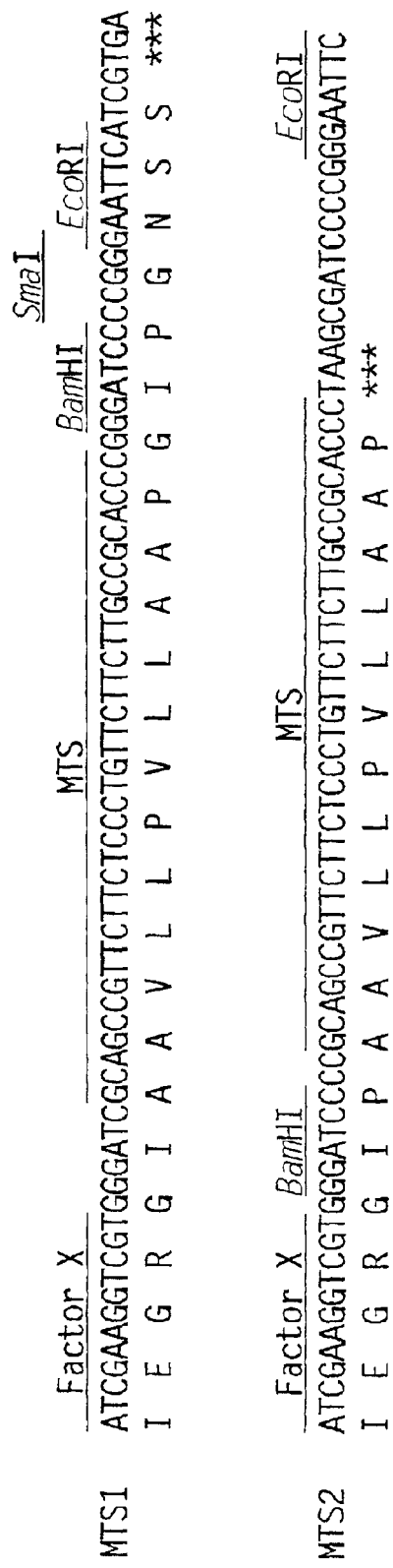
FIG. 1 shows the nucleotide and derived amino acid sequences of the membrane-translocating sequence inserted into pGEX-3X to form the expression vectors pGEX-3X-MTS 1 (MTS1) (nucleotide sequence SEQ ID NO: 19; amino acid sequence SEQ ID NO: 20) and pGEX-3X-MTS2 (MTS2) (nucleotide sequence SEQ ID NO: 21: amino acid sequence SEQ ID NO: 22).
Figure 2:
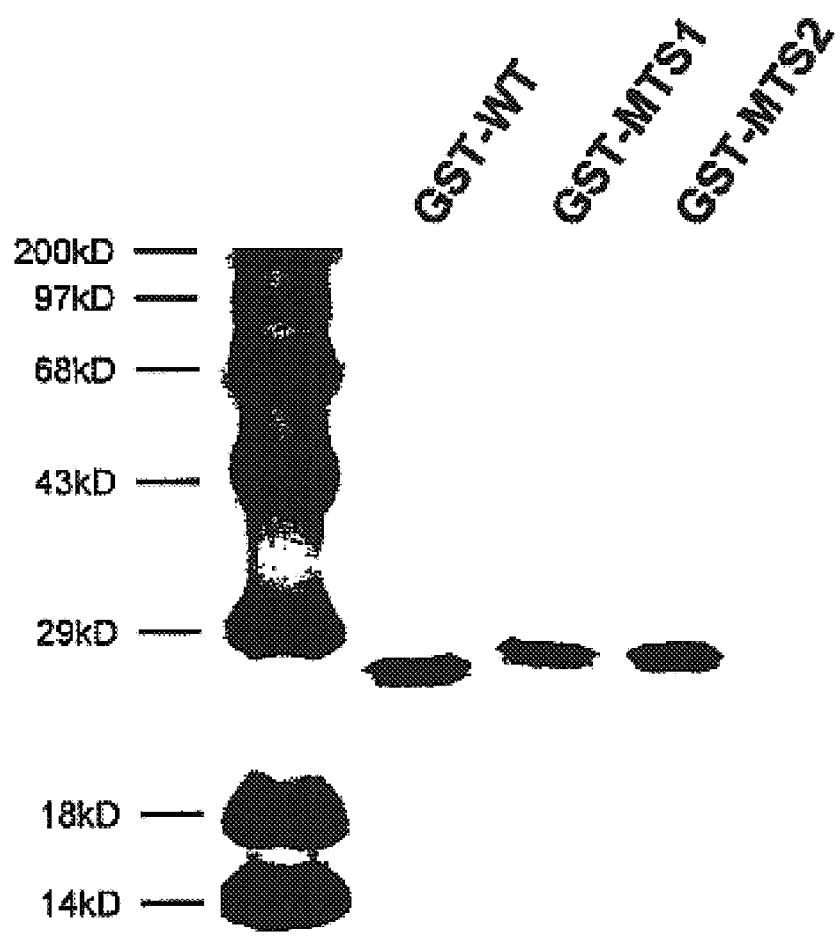
FIG. 2 illustrates analysis of purified preparations of wild-type glutathione S-transferase (WT-GST), GST-MTS1 fusion protein, and GST-MTS2 fusion protein by sodium dodecyl sulfate-polyacrylamide gel electrophoresis (SDS-PAGE). Two micrograms of each protein were separated by 12% SDS-PAGE and stained with Coomassie brilliant blue.
Figure 3A:
FIG. 3a, FIG. 3b, and FIG. 3c.
Figure 3B:
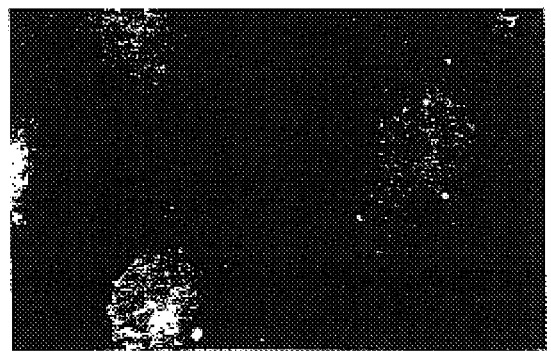
Figure 3C:
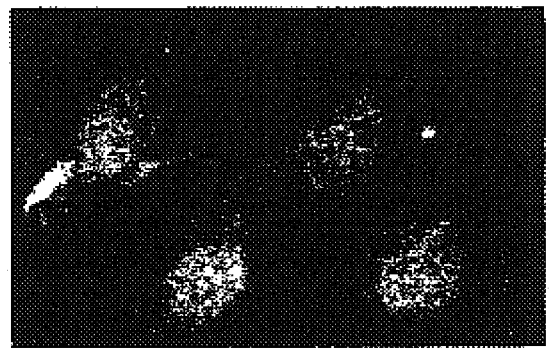
Figure 4:
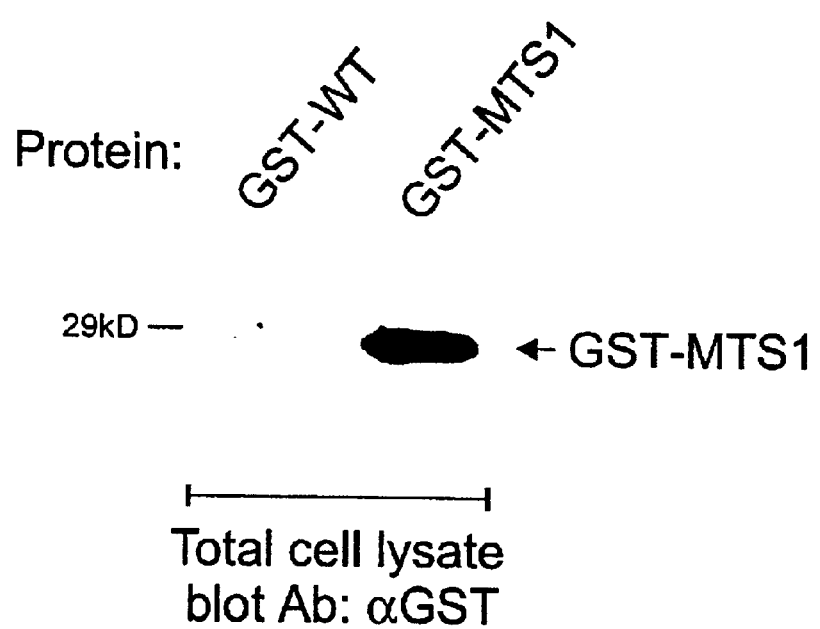
FIG. 4 shows Western blot of cell lysates from NIH 3T3 cells treated with GST-MTS1 or GST-WT. The antibody used fo protein detection was anti-glutathione S-transferase.
Figure 5:
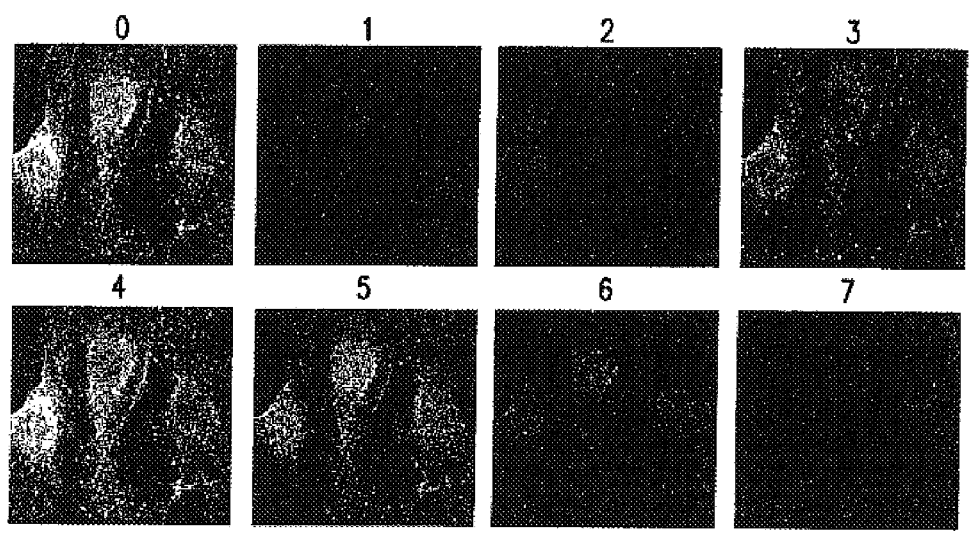
FIG. 5 shows confocal laser scanning microscope of NIH 3T3 cells treated with 20 μM of GST-MTS1 protein for 30 minutes. Protein was detected as yellow fluorescent signals by indirect immunofluorescence assay and analyzed by a six-step Z-position sectional scanning of the cell. Panels 1–7: 1 μm cell sections from the bottom to the top of representative GST-MTS1-treated cells. 0: the composite image of all seven sections.
Figure 6A:
FIG. 6a, FIG. 6b, and FIG. 6c.
Figure 6B:
Figure 6C:

Previous efforts to import small peptides into a cell have been successful, but efforts to import larger polypeptides or whole proteins have not. The present invention seeks to overcome the shortcomings of the prior art by providing a peptide capable of directing the import of polypeptides and proteins into a cell. It is to be understood that, as used herein, polypeptide is intended to encompass any amino acid sequence comprising more than three amino acids, and includes particularly protein domains and proteins.

The present invention relates to a membrane-translocating peptide and its use in mediating membrane-translocation and import of a polypeptide, protein domain, or full-length protein into a cell. The inventors have synthesized an artificial membrane translocation sequence (MTS) of 12 amino acids for protein import, and have used a DNA sequence encoding this 12-amino acid peptide to construct a plasmid expression vector for genetically engineering proteins with cell membrane permeability by expressing the 12 amino acid MTS as a fusion with a target protein for import into the cell. In the preferred embodiment of the present invention, the amino acid sequence of the 12-residue membrane-translocating peptide is Ala-Ala-Val-Leu-Leu- Pro-Val-Leu-Leu-Ala-Ala-Pro (SEQ ID NO: 1). As used herein, however, the term "peptide" is intended to include mimetics and the term "amino acid" is intended to include D-form amino acids and modified amino acids. These substitutions may be made by someone of skill in the art, using the known structural similarities between the molecules. The membrane translocating sequence may be located immediately adjacent to, or some distance from, the cargo protein as produced by the recombinant nucleotide vector of the present invention. Therefore, the amino acid sequence is also intended to include any peptide or protein sequence that may include additional amino acids either N-terminal or C-terminal to the listed sequence, or both.

The amino acid sequence is also intended to include an MTS comprising fewer than twelve residues, as signal peptide sequences of as few as eight amino acids provide membrane translocation of peptides across membranes within the cell. In the present invention, an alternative MTS comprised of an amino acid sequence of eight (8) to twelve (12) consecutive amino acids chosen from SEQ ID NO: 1. Exemplary of such alternative MTS sequences are Ala-Ala-Val-Leu-Leu-Pro-Val-Leu (SEQ ID NO: 2), Ala-Ala-Val-Leu-Leu-Pro-Val-Leu-Leu (SEQ ID NO: 3), Ala-Ala-Val-Leu-Leu-Pro-Val-Leu-Leu-Ala (SEQ ID NO: 4), Ala-Ala-Val-Leu-Leu-Pro-Val-Leu-Leu-Ala-Ala (SEQ ID NO: 5), Leu-Pro-Val-Leu-Leu-Ala-Ala-Pro (SEQ ID NO: 6), Leu-Leu-Pro-Val-Leu-Leu-Ala-Ala-Pro (SEQ ID NO: 7), Val-Leu-Leu-Pro-Val-Leu-Leu-Ala-Ala-Pro (SEQ ID NO: 8), and Ala-Val-Leu-Leu-Pro-Val-Leu-Leu-Ala-Ala-Pro (SEQ ID NO: 9). Alternative MTS sequences are intended to include alternative amino acids, as well as additional C-terminal or N-terminal amino acids as described for SEQ ID NO: 1.

In a second preferred embodiment of the invention, the DNA coding sequence for the membrane-translocating peptide is
5'GCAGCCGTTCTTCTCCCTGTTCTTCTTGCCGCACCC-3' (SEQ ID NO: 10).
Alternate embodiments include, but are not limited to:

It is to be understood that amino acid and nucleic acid sequences may include additional residues, particularly N- or C-terminal amino acids or 5' or 3' nucleotide sequences, and still be essentially as set forth in the sequences disclosed herein, as long as the sequence confers membrane permeability upon the polypeptide or protein moiety of the fusion protein.

A nucleic acid fragment of almost any length may be employed, and may be combined with other DNA sequences, such as promoters, polyadenylation signals, additional restriction enzyme sites, multiple cloning sites, other coding segments, and the like. Therefore, overall length may vary considerably.

In the method of the present invention, the nucleotide sequence described above is inserted into a protein expression vector to produce a protein which can be imported from the exterior to the interior of a cell by the action of the membrane translocating sequence described herein.

Genetically Engineering a Protein with Cell Membrane Permeability

In a preferred embodiment of the present invention, a protein expression vector is genetically engineered to incorporate a DNA sequence encoding a membrane translocating sequence in an orientation either N-terminal or C-terminal to the DNA sequence encoding the peptide, polypeptide, protein domain, or full-length protein of interest, and in correct reading frame so that a fusion protein consisting of the membrane translocating peptide and the target peptide, polypeptide, protein domain, or full-length protein may be expressed. It is understood by those of skill in the art that all protein domains and full-length proteins are polypeptides, being formed of a series of peptide linkages. Therefore, as used herein, the term "polypeptide" will be used to denote an amino acid sequence of more than 25 amino acids, and the term "peptide" will be used to denote an amino acid sequence of 25 amino acids or less. In the preferred embodiment of the method of genetically-engineering proteins with cell membrane permeability as described in the present invention, the membrane-translocating peptide is an MTS of the present invention. In alternate embodiments of the

```
5'GCAGCCGTTCTTCTCCCTGTTCTT-3'            (SEQ ID NO: 11);

5'-GCAGCCGTTCTTCTCCCTGTTCTTCTT-3'        (SEQ ID NO: 12);

5'-GCAGCCGTTCTTCTCCCTGTTCTTCTTGCC-3'     (SEQ ID NO: 13);

5-GCAGCCGTTCTTCTCCCTGTTCTTCTTGCCGCA-3'   (SEQ ID NO: 14);

5'-CTCCCTGTTCTTCTTGCCGCACCC-3'           (SEQ ID NO: 15);

5'-CTTCTCCCTGTTCTTCTTGCCGCACCC-3'        (SEQ ID NO: 16);

5'-GTTCTTCTCCCTGTTCTTCTTGCCGCACCC-3'     (SEQ ID NO: 17); and

5'-GCCGTTCTTCTCCCTGTTCTTCTTGCCGCACCC-3'  (SEQ ID NO: 18).
```

It is well known in the art, however, that a single amino acid may be encoded by more than one nucleotide codon— and that the nucleotide sequence may be easily modified to produce an alternate nucleotide sequence that encodes the same peptide. Therefore, alternate embodiments of the present invention include alternate DNA sequences encoding peptides containing the amino acid sequences as previously described. DNA sequences encoding peptides containing the claimed amino acid sequence include DNA sequences which encode any combination of the claimed sequence and any other amino acids located N-terminal or C-terminal to the claimed amino acid sequence.

present method of genetically engineering proteins with membrane translocating activity, the MTS may comprise an alternate sequence which mediates the import of a peptide or polypeptide through the cell membrane to the interior of a cell.

In a further embodiment of the invention, a cleavage site is located between the MTS and the target polypeptide, protein domain, or full-length protein. This site may alternatively be a factor X site, or other site that is known to those of skill in the art to effect the cleavage of the fusion protein to physically remove the MTS from the subject peptide or polypeptide. As used herein, an MTS is a membrane translocating sequence of the present invention, which directs cellular transport of a target protein from the exterior to the interior of a cell. A target protein is a protein which normally evidences less than optimal permeability through the cell membrane, but which, when linked either N-terminal or C-terminal to an MTS of the present invention, is transported from the exterior to the interior of the cell.

The MTS of the present invention, and the method of genetically engineering proteins for cell membrane permeability, can be used in a variety of applications, including, but not limited to, studies of intracellular protein function, vaccine delivery, and delivery of peptides, nucleic acids, and other organic compounds for therapeutic use. A specific example of a polypeptide involved in intracellular signaling is the SH2 domain of the Grb2 protein that becomes bound to tyrosine-phosphorylated epidermal growth factor receptor (EGFR). A specific example of a viral protein is the Hepatitis B surface antigen, or the human immunodeficiency virus type 1 HXB-2 envelope glycoprotein. The MTS of the present invention has been shown thus far to mediate the cellular import of an entire 120-kDa protein fusion product. Other proteins that can be delivered to the interior of the cell using the method of the present invention include, but are not limited to, MAP kinase, RAS, caspases, protein members of the Bcl-2 family, Bax, NFκB, green fluorescent protein (GFP) and STAT.

The method of the present invention provides a means of producing proteins with cell permeability for introduction into the interior of the cell, where their actions help to further elucidate cellular control and biosynthesis mechanisms. This method also provides a means to introduce intracellular proteins into cells to produce targeted cellular changes, such as inhibition of apoptosis by the introduction of Bcl-2. Cell cycle control, for example, can be altered by the introduction of a functional p53 protein product into those cells that have become tumorigenic due to an abnormal p53 protein.

Expression system vectors, which incorporate the necessary regulatory elements for protein expression, as well as restriction endonuclease sites that facilitate cloning of the desired sequences into the vector, are known to those of skill in the art. A number of these expression vectors are commercially available. In a preferred embodiment of the present invention, the expression vector is pGEX-3X (Amersham Pharmacia, Piscataway, N.J.), U.S. Pat. No. 6,654,176 (Smith, et al., incorporated herein by reference), which comprises a nucleotide sequence encoding a fusion protein including glutathione-S-transferase. Insertion of a nucleotide sequence encoding an MTS as described by the present invention into vector pGEX-3x, either 5' or 3' to the glutathione-S-transferase (GST) gene of the vector enables expression of a fusion protein incorporating both the MTS and the glutathione-S-transferase protein. The MTS, connected either N-terminal or C-terminal to the glutathione-S-transferase protein, carries the GST protein membrane to the interior of the cell.

In another preferred embodiment of the present invention, an alternate recombinant DNA expression vector containing the elements previously described is introduced into an appropriate host cell where cellular mechanisms of the host cell direct the expression of the fusion protein encoded by the recombinant DNA expression vector. Alternately, cell-free systems known to those of skill in the art can be chosen for expression of the fusion protein.

The purified fusion protein produced by the expression vector host cell system can then be administered to the target cell, where the membrane-translocating sequence mediates the import of the fusion protein through the cell membrane of the target cell into the interior of the cell.

An expression vector host cell system can be chosen from among a number of such systems that are known to those of skill in the art. In one embodiment of the invention, the fusion protein can be expressed in *Escherichia coli*. In alternate embodiments of the present invention, fusion proteins may be expressed in other bacterial expression systems, viral expression systems, eukaryotic expression systems, or cell-free expression systems. Cellular hosts used by those of skill in the art include, but are not limited to, *Bacillus subtilis*, yeast such as *Saccharomyces cerevisiae, Saccharomyces carlsbergenesis, Saccharomyces pombe*, and *Pichia pastoris*, as well as mammalian cells such as 3T3, HeLa, and Vero. The expression vector chosen by one of skill in the art will include promoter elements and other regulatory elements appropriate for the host cell or cell-free system in which the fusion protein will be expressed. In mammalian expression systems, for example, suitable expression vectors can include DNA plasmids, DNA viruses, and RNA viruses. In bacterial expression systems, suitable vectors can include plasmid DNA and bacteriophage vectors.

Examples of specific expression vector systems include the pBAD/gIII vector (Invitrogen, Carlsbad, Calif.) system for protein expression in *E. coli*, which is regulated by the transcriptional regulator AraC. Dose-dependent induction enables identification of optimal expression conditions for the specific target protein to be expressed. By inserting the polynucleotide sequence of the membrane translocating sequence of the present invention either 5' or 3' to the polynucleotide sequence of a target protein, this vector can be used to express a number of fusion proteins for which optimal expression conditions may vary. Furthermore, the vector encodes the polyhistidine (6×His) sequence and an epitope tag to allow rapid purification of the fusion protein with a nickel-chelating resin, along with protein detection with specific antibodies to detect the presence of the secreted protein.

An example of a vector for mammalian expression is the pcDNA3.1/V5-His-TOPO eukaryotic expression vector (Invitrogen). In this vector, the fusion protein can be expressed at high levels under the control of a strong cytomegalovirus (CMV) promoter. A C-terminal polyhistidine (6×His) tag enables fusion protein purification using nickel-chelating resin. Secreted protein produced by this vector can be detected using an anti-His (C-term) antibody.

Another example of a protein expression vector for a mammalian expression system is the pEBVHis (Invitrogen) vector. There are three different versions of this vector (pEBVHis A, pEBVHis B, and pEBVHis C), that differ in spacing between the sequences that code for the N-terminal peptide and the multiple cloning site. The vector can therefore be chosen to facilitate cloning the target polypeptide nucleotide sequence into the vector in correct reading frame to produce a biologically functional polypeptide. The multiple cloning has nine unique restriction sites, including BamHI, XhoI, Bgl II, Pvu II, Kpn I, Hind III, Not I, Sfi I, and Cla I to facilitate insertion of the nucleotide sequences for production of the MTS/target polypeptide fusion. The vector includes an Epstein-Barr virus origin of replication, and the Epstein-Barr virus encoded nuclear antigen (EBNA-1) which transactivates the origin of replication to allow the vector DNA to replicate episomally when transfected into an appropriate mammalian cell line. Appropriate cell lines for this vector include 293 cells, 293-EBNA, COS, or CV-1. The Rous Sarcoma virus long terminal repeat directs transcription of the fusion protein in this vector, and selection in mammalian cells is facilitated by the Hygromycin B drug resistance marker under the control of the thymidine kinase promoter in the vector. Purification of the fusion protein can be accomplished using metal affinity chromatography to bind the polyhistidine tag, and the tag can be subsequently cleaved from the fusion protein using an enterokinase cleavage recognition sequence.

A baculovirus expression system can also be used for production of a fusion protein comprising the MTS and a target protein. A commonly used baculovirus is AcMNPV. Cloning of the MTS/target protein DNA can be accomplished by using homologous recombination. The MTS/target protein DNA sequence is cloned into a transfer vector containing a baculovirus promoter flanked by baculovirus DNA, particularly DNA from the polyhedrin gene. This DNA is transfected into insect cells, where homologous recombination occurs to insert the MTS/target protein into the genome of the parent virus. Recombinants are identified by altered plaque morphology.

Many fusion proteins containing target proteins that may not be appropriately post-translationally modified in bacterial expression systems can be expressed with baculovirus vectors. In a method for generating recombinant baculovirus, the MTS/target protein DNA is cloned into donor plasmid, such as the pFastBac donor plasmid of the Bac-to-Bac™ Baculovirus Expression System (GibcoBRL). The recombinant plasmid is then transformed into *E. coli* host cells that contain a bacmid with a mini-attTn7 target site and helper plasmid. The mini-Tn7 element on the donor plasmid can transpose to the mini-attTn7 target site on the bacmid in the presence of helper plasmid transposition proteins. Transposition results in disruption of the lacZα gene, allowing identification of colonies containing recombinant bacmids. Recombinant bacmid DNA is then used to transfect insect cells, such as *Spodoptera frugiperda* cell Sf9. By using a histidine tag expression vector, such as the pFastBacHT expression vector (Gibco BRL), the expressed fusion protein can be purified using the 6xHis tag.

Enzymes, signaling molecules, mediators of cell cycle control, transcription factors, antigenic peptides, full-length protein products of viral, bacterial, or other origin for use in vaccine therapy, protein products of human cells for use in cancer vaccine therapy, toxins, and proteins involved in intracellular signaling systems which may not be appropriately post-translationally modified in bacterial expression systems can be expressed with baculovirus vectors.

Proteins as described above can also be produced in the method of the present invention by mammalian viral expression systems. The Sindbis viral expression system, for example, can be used to express the fusion protein at high levels. Sindbis vectors have been described, for example, in U.S. Pat. No. 5,091,309 (Schlesinger et al.), incorporated herein by reference. Sindbis expression vectors, such as pSinHis (Invitrogen, Carlsbad, Calif.) can be used to express the fusion protein under the direction of the subgenomic promoter PSG. In vitro transcribed RNA molecules encoding the fusion protein and the Sindbis proteins required for in vivo RNA amplification can be electroporated into baby hamster kidney (BHK) cells using methods known to those of skill in the art. Alternatively, the RNA encoding the fusion protein and Sindbis proteins required for in vivo RNA amplification can be cotransfected with helper RNA that permits the production of recombinant viral particles. Viral particles containing genetic material encoding the fusion protein can then be used to infect cells of a wide variety of cell types, including mammalian, avian, reptilian, and Drosophila. Fusion protein expressed from the pSinHis (Invitrogen) vector can be detected with antibody to an Anti-Xpress™ epitope encoded by the vector sequence. The pSinHis vector also includes a polyhistidine tag which provides a binding site for metal-chelating resins to facilitate purification of the expressed fusion protein. Furthermore, an enterokinase cleavage site located between the histidine tag and the fusion protein allows the histidine tag to be enzymatically removed following purification.

An ecdysone-inducible mammalian expression system (Invitrogen, Carlsbad, Calif.), described by No, et al. (1996) can also be used to express the MTS/target fusion protein. Vectors used in the ecdysone-inducible mammalian expression system can be organized to produce cell-permeable target proteins by expressing the MTS/target fusion protein from the expression cassette. With the ecdysone-inducible system, higher levels of protein production can be achieved by use of the insect hormone 20-OH ecdysone to activate gene expression via the ecdysone receptor. An inducible expression plasmid provides a multiple cloning site, into which the nucleotide sequence of the MTS and a target protein can be ligated, oriented so that the MTS is translated either N-terminal or C-terminal to the target protein in the expressed fusion protein. The expression vector contains ecdysone response elements upstream of the promoter (a minimal heat shock promoter) and the multiple cloning site. Cotransfection of a second plasmid, pVgRXR (Invitrogen), provides the receptor subunits to make the cell responsive to the steroid hormone ecdysone analog, ponasterone A. A control expression plasmid containing the lacZ gene can be cotransfected with pVgRXR to provide a marker for transfected cells. Upon induction with ponasterone A, the control plasmid expresses β-galactosidase. Cotransfection of the inducible expression construct and pVgRXR into the mammalian cell of choice can be accomplished by any of the standard means known to those of skill in the art. These include, for example, calcium phosphate transfection, lipid-mediated transfection, and electroporation. Levels of expression of the fusion protein in this system can be varied according to the concentration and length of exposure to ponasterone. Stable cell lines that constitutively express the MTS/target fusion protein can be established using Zeocin™ (Invitrogen), a bleomycin/phleomycin-type antibiotic isolated from Streptomyces, and neomycin or hygromycin.

Yeast host cells, such as *Pichia pastoris*, can also be used for the production of a genetically engineered cell permeable protein by the method of the present invention. Expression of heterologous proteins from plasmids transformed into Pichia has previously been described by Sreekrishna, et al. (U.S. Pat. No. 5,002,876, incorporated herein by reference). Vectors for expression in Pichia of a fusion protein comprising an MTS of the present invention and a target protein are commercially available as part of a Pichia Expression kit (Invitrogen, Carlsbad, Calif.). *Pichia pastoris* is a methylotrophic yeast, which produces large amounts of alcohol oxidase to avoid the toxicity of hydrogen peroxide produced as a result of methanol metabolism. Alcohol oxidase gene expression is tightly regulated by the AOX1 and AOX2 promoters. In Pichia expression vectors, high levels of expression are produced under the control of these promoters. Ohi, et al. U.S. Pat. No. 5,683,893, incorporated herein by reference) have previously described a mutant AOX2 promoter capable of producing enhanced expression levels. Using previously described and commercially available Pichia expression vectors, a target protein can be genetically engineered for cell permeability by incorporating into the expression vector both the nucleotide sequence of the target protein and a nucleotide sequence encoding an MTS of the present invention. The nucleotide sequence encoding an MTS can be incorporated into the vector either 5' or 3' to the nucleotide sequence encoding the target protein. Under the control of the AOX2 or AOX2 promoter, high levels of protein can be expressed.

Purification of heterologous protein produced in Pichia has been described by Craig, et al. (U.S. Pat. No. 5,004,688, incorporated herein by reference), and techniques for protein purification from yeast expression systems are well known to those of skill in the art. In the Pichia system, commercially available vectors can be chosen from among those that are more suited for the production of cytosolic, non-glycosylated proteins and those that are more suited for the production of secreted, glycosylated proteins, or those directed to an intracellular organelle, so that appropriate protein expression can be optimized for the target protein of choice.

Peptide Attachment Using Covalent Linkage

The MTS of the present can also be used to increase cell membrane permeability of a polypeptide, oligonucleotide, or other organic molecule by attaching the MTS to the target molecule by means of a covalent attachment. Orthogonal coupling methods for peptides and polypeptides involving a thioester intermediate have been described by Tam, et al. (1995).

Therapeutic use of oligonucleotides is often hindered by their low cellular permeability. Although oligonucleotides have been shown to be taken up by cells via an endocytic process, oligonucleotides that enter the cell in this manner are usually trapped in endocytic vesicles and degraded in lysosomes. Dokka et al. (1997) have demonstrated non-endocytic uptake of oligonucleotides using a signal import peptide consisting of the hydrophobic sequence of Kaposi fibroblast growth factor signal peptide (Ala-Ala-Val-Ala-Leu-Leu-Pro-Ala-Val-Leu-Leu-Ala-Leu-Leu-Ala-Pro) (SEQ ID NO: 23) covalently conjugated to a polycationic linker, poly-L-lysine (PL). The poly-L-lysine linker was further complexed electrostatically to the polyanionic backbone of the oligonucleotide. The signal peptide/poly-L-lysine linker was synthesized using the standard Fmoc procedure.

The MTS of the present invention provides efficient transport of large protein molecules across the cell membrane, whereas other membrane transport peptides previously tested have not been demonstrated to transport molecules of size greater than approximately 25 amino acids. An MTS as described herein can be attached to a peptide or polypeptide using methods, such as those described by Tam et al., to enhance peptide or polypeptide membrane permeability. The MTS can be provided in the form of a kit, including the necessary components known to those of skill in the art to facilitate linkage of a peptide to a target polypeptide. A target protein linked to the MTS in this manner can then be delivered to the cell either in vitro or in vivo for intracellular import.

An MTS of the present invention can also be provided as a fusion between the MTS and a poly-L-lysine linker. When this fusion product is mixed with oligonucleotide, as described by Dokka, et al., the poly-L-lysine linker can complex electrostatically with the polyanionic backbone of the oligonucleotide. The MTS-PL linker-oligonucleotide complex can then be administered in vitro or in vivo to deliver the oligonucleotide to the interior of the cells.

Conditions for Protein Import Into a Target Cell

Suitable conditions for protein import into the cell mediated by the membrane-translocating peptide of the present invention include incubating the cells in an extracellular concentration of fusion protein in the 20 $\mu$M range at 37° C.
for 30 minutes, to accomplish the import of approximately 0.5–1×10$^6$ molecules of transported protein per cell. Effective concentrations, however, may vary with differing proteins and cell types, and may be considered as amounts sufficient to result in import of fusion proteins into the cell, with protein import exhibiting dose-dependence. Methods for providing sufficient concentration to achieve protein import are known to those of skill in the art. Suitable import temperatures include temperatures in a preferred range between 22° C. and 37° C.

The fusion protein produced by the method of the present invention may be administered in vitro by any of the standard methods known to those of skill in the art, such as addition of fusion protein to culture medium, or other methods as described by Lin et al., U.S. Pat. No. 5,807,746, incorporated herein by reference. Furthermore, it will be appreciated by those of skill in the art that fusion proteins produced by this method may be delivered in vivo by standard methods utilized for protein/drug delivery, including parenteral administration, intravenous administration, topical administration, aerosol administration or inhalation, oral administration (particularly when provided in encapsulated form), or by rectal or vaginal administration (particularly when provided in suppository form).

Administration of fusion protein produced by the method of the present invention may be performed for a time length of from 30 minutes to 18 hours, particularly when administration is accomplished by addition of fusion protein to culture media for in vitro use. For in vivo or in vitro use, effective administration time for a fusion protein produced by the method of the present invention may be readily determined by one of skill in the relevant art.

Uptake of the fusion protein is dependent upon the external concentration of the fusion protein and the period of application, therefore the internal concentration of protein can be controlled by controlling administration to the extracellular environment. At an extracellular concentration of 20 $\mu$M, NIH 3T3 cells, for example, receive up to 10$^6$ molecules of protein per cell over a 60-minute period, resulting in an internal concentration of approximately 2 $\mu$M.

Studying Intracellular Proteins Using MTS and Molecular Labeling

Molecular labeling techniques have previously been described for studying intracellular protein function. Jones, et al. (1998) describe a method of molecular labeling using intracellular expression of a fusion protein comprising green fluorescent protein (GFP) and dynamin. Kohler, et al. (1997) describe a method of studying exchange of protein molecules through the connections between plastids of higher plants. The molecular exchange was visualized using green fluorescent protein (GFP) to label the plastid stroma. In fact, GFP from *Aequorea victoria* has been genetically fused with many host proteins to produce fluorescent chimeras (reviewed by Tsien, 1998). Griffin, et al. (1998) describe a method of incorporating a small receptor domain, utilizing four cysteines at the i, i+1, i+4, and i+5 positions of an α-helix, to create a ligand for 4',5'-bis(1,3,2-dithioarsolan-2-yl)fluorescein, which is membrane-permeant and non-fluorescent until it binds with high affinity and specificity to the tetracysteine domain. This in situ labeling technique provides greater versatility in attachment sites and eliminates the potentially disruptive effects of GFP (a 238 amino acid protein) in the cell.

Olsen, et al., (1995) describe a method of analyzing MAP4 function in living cells using a GFP-MAP4 chimera. Expression of the GFP-MAP4 chimera in dividing cells enabled visualization of MAP4 in microtubule organization.

Rizzuto, et al. (1995) describe a modified GFP cDNA that includes a mitochondrial targeting sequence. Expression of the cDNA construct in the cells allows visualization of mitochondrial movement within living cells.

The techniques previously described, however, rely upon protein expression within the target cell using polynucleotide vectors. The MTS of the present invention, and the method of genetically engineering proteins for membrane permeability, provides a more efficient method for studying intracellular protein function by producing a fusion protein comprising the MTS, a protein label (such as GFP of the tetracysteine domain described by Griffin), and the protein to be studied. The fusion protein can be produced in a system such as those described previously, and the purified fusion protein can be administered to the cells. Once administered to the extracellular environment, the MTS directs import of the chimeric protein into the interior of the cell and the molecular marker enables visualization of target protein localization.

Other markers that may be used in the method of the present invention include, but are not limited to, rhodamine, biotinylated markers, and blue fluorescent protein. Vector systems providing the polynucleotide coding sequence for green or blue fluorescent proteins are available from Aurora Biosciences (San Diego, Calif.), Clontech (Palo Alto, Calif.), and Quantum Biotechnologies (Montreal, Canada). Multiple cloning sites within these vectors enable insertion of the MTS of the present invention either N-terminal or C-terminal to the label/target protein chimera.

The method previously described can also be used to label cells to facilitate observation of, for example, cellular migration through tissue and tumor metastasis. An MTS/GFP/target protein chimera can be administered to cells prior to injection in situ, or can be administered locally in situ, in the case of tumor cells, to study metastasis. Methods for studying cellular migration are known to those of skill in the art. These methods are facilitated by the method of the present invention, producing a chimeric protein which labels the cell with a protein that is easily detectable, cell-permeable, and therefore located in the interior of the cell due to the presence of the MTS either C-terminal or N-terminal to the GFP or target protein sequence.

Vaccine Administration Using Membrane Translocating Sequences and Genetically Engineered Proteins Vaccines provide the most effective means of control of infectious disease. Deaths from infectious diseases rose 22 percent between 1980 and 1992 (not including deaths attributable to HIV, the virus which causes acquired immunodeficiency syndrome). In an effort to reduce the prevalence of infectious disease and decrease the risks associated with vaccination with killed or attenuated live organisms, scientists have focused on the development of peptide vaccines and DNA vaccines. Organisms for which antigenic proteins have been identified include Haemophilus influenzae B, *Clostridium difficile, Helicobacter pylori*, meningococcus, and *Borrelia burgdorferi*, to name only a few. For example, the 31 kD antigen OspA and 34 kD antigen OspB of *Borrelia burgdorferi* have been demonstrated to provide a sufficient protective response to provide the incentive to begin the required FDA vaccine trials for a lyme disease vaccine using these protein antigens. Viruses for which vaccines are currently being developed include human immunodeficiency virus (HIV), Ebola, influenza, cytomegalovirus, Epstein-Barr virus, herpes simplex, human papillomavirus, parainfluenza type 3, and B19 parvovirus. Recombinant vaccines, often utilizing viral vectors, have provided the most promising vector for antigen delivery. However, administration requires administration of the vector rather than just the protein product. The viral vectors have proven to present safety issues which often limit their use.

Viral vaccines, although effective, often pose serious problems in terms of delivery and in terms of control of transmission. Foot-and-mouth disease virus (FMDV), for example, is a highly contagious viral disease of pigs and cattle. Inactivated virus vaccines are effective, but outbreaks of the disease have been directly associated with incomplete inactivation of virus or the escape of virus from vaccine manufacturing facilities (King et al., 1981). Efforts have therefore been directed toward the development of DNA vaccines, which produce isolated proteins of the infectious agent and eliminate the possibility of reversion to virulence. Chinsamgaram, et al. (1998) developed a DNA inoculation-based strategy to utilize plasmid DNA to produce non-infectious viral capsids in inoculated animals. Inoculated animals subsequently developed antibodies to the capsid proteins, providing a protective response. Chen, et al. (1998) demonstrated that PLG-encapsulated rotavirus VP6 DNA produced a protective response after oral administration in BALB/c mice.

U.S. Pat. No. 5,703,057, issued to Johnston et al. (incorporated herein by reference), describes the use of vaccines based upon expression libraries constructed from fragmented genomic DNA of pathogens. Once transfected into the host cell, the proteins derived from the DNA sequences are produced. Advantages of this technique include: (1) production of vaccines without having to pre-determine which specific proteins are responsible for eliciting protection; (2) presentation of peptides which might normally be hidden by immune-avoidance mechanisms in the killed or attenuated host organism; (3) presentation of whole protein antigens in a manner similar to that achieved by live/attenuated vaccines; (4) modification of the vaccine composition to utilize only those antigenic proteins found to be most effective; and (5) introduction of antigens into cells which might normally not be affected by live/attenuated organisms. These same advantages are inherent in the present invention. Peptide vaccines of the present invention, however, provide the further advantage of providing a polypeptide or protein to the cell without requiring administration of a recombinant vector, which may or may not provide efficient protein production.

Peptide delivery has been accomplished by a variety of means, including encapsulation, and has been demonstrated to produce a sufficient antigenic response to provide protection. Peptide vaccines, however, require identification of specific antigenic epitopes in order to synthesize the appropriate peptide for vaccine use. Immunization with a complete protein or protein domain provides a method for introducing epitopes into the cell without having to first isolate the peptides containing them. The antigen-processing machinery of the cell then provides the antigen processing necessary to invoke a protective immune response.

Synthetic peptides from the envelope glycoprotein sequence of Murray Valley encephalitis (MVE) virus have been shown by Mathews, et al. (1992) to induce antibody and in vitro proliferation of peptide-primed helper T (Th) cells. In dogs, a synthetic peptide vaccine has been demonstrated to protect dogs against challenge with virulent canine parvovirus (Langeveld, et al. 1994)

Methods for preparation of vaccines containing peptide sequences as active ingredients are well known in the art. Such methods are exemplified in U.S. Pat. Nos. 4,578,770; 4,596,792; 4,599,230; 4,599,231; 4,608,251; and 4,601,903, all incorporated herein by reference. These methods can also be used to prepare vaccines using cell-permeable polypeptides and proteins.

Vaccines using cell-permeable polypeptides provide an advantage over peptide vaccines. Immune system recognition of antigen depends upon appropriate antigen processing. Previously, entire proteins or protein domains could not be delivered to the interior of the cell for processing to occur. As a consequence, peptides representing antigenic epitopes had to be identified prior to delivery to the cell of small peptides representing those epitopes. The method of the present invention allows whole proteins or protein domains to be imported into the cell, where antigenic processing can occur. This provides multiple antigenic epitopes in one administration, and eliminates the need for experimental identification of specific epitopes for vaccine development.

Typically, such vaccines are prepared for injection into a human or mammalian subject. Injectable vaccines can be prepared as liquid solutions or suspensions. Solid forms can be prepared which are suitable for solution in, or suspension in, liquid prior to injection. The preparation may also be emulsified. The active immunogenic ingredient is often mixed with a pharmaceutically acceptable carrier which is compatible with the active ingredient. Suitable carriers include, but are not limited to, water, dextrose, glycerol, saline, ethanol, and combinations thereof. The vaccine may contain additional agents such as wetting or emulsifying agents, pH buffering agents, or adjuvants which enhance the effectiveness of the vaccine.

The vaccine may be conventionally administered parenterally. Either subcutaneous or intramuscular injection is appropriate. Other modes of administration may include oral administration, nasal administration, rectal administration, and vaginal administration, which may involve combining the peptide immunogen with pharmaceutically acceptable carriers such as mannitol, lactose, starch, magnesium stearate, sodium saccharine, cellulose, magnesium carbonate, or other carrier. Compositions for oral administration may form solutions, suspensions, tablets, pills, capsules, sustained release formulations or powders. A protein-based vaccine of the present invention can be administered by enteric-coated capsule for release of the polypeptide into the lumen of the intestine.

The peptides of the present invention may be formulated into the vaccine as neutral or salt forms. Pharmaceutically acceptable salts include the acid addition salts (formed with the free amino groups of the polypeptide) and which are formed with inorganic acids such as, for example, hydrochloric or phosphoric acids, or such organic acids as acetic, mandelic, oxalic, and tartaric. Salts formed with the free carboxyl groups may also be derived from inorganic bases such as, for example, sodium, potassium ammonium, calcium, or ferric hydroxides, and such organic bases as isopropylamine, trimethylamine, 2-ethylamino ethanol, and histidine.

The vaccine is administered in a manner compatible with the dosage formulation, and in such amount as will be therapeutically effective and immunogenic. The quantity to be administered depends on the subject to be treated, taking into account, for example, the capacity of the individual's immune system to synthesize antibodies, and the degree of protection desired. Precise amounts of active ingredient (peptide immunogen) to be administered depend on the judgment of the practitioner. Suitable dosage ranges generally require several hundred micrograms of active ingredient per vaccination. Also variable are regimes for initial administration and booster vaccinations, which should be determined by the judgment of the practitioner. Dosage of vaccine will depend on the route of administration and will vary according to the size of the host.

Adjuvants for use in combination with the polypeptide immunogen of the present invention for vaccination include, but are not limited to, aluminum hydroxide or phosphate, also known as alum, commonly used as 0.05 to 0.1 percent solution; aggregation of the protein in the vaccine by heat treatment with temperatures ranging between 70° for 30 seconds to 101° C. for 2 minutes.

Methods for producing the hepatitis B surface antigen (HBsAg) in yeast have been described previously in U.S. Pat. No. 4,769,238 issued to Rutter, et al., U.S. Pat. No. 4,895,800 issued to Tschopp, et al., and U.S. Pat. No. 5,098,704 issued to Valenzuela (all incorporated herein by reference). Using the method of the present invention, HBsAg can be produced in yeast, such as *Pichia pastoris*, as a fusion protein containing the membrane translocating sequence (MTS) either N-terminal or C-terminal to the HbsAg protein. The purified fusion product can then be administered as a protein vaccine, capable of entering the cell for antigen-processing by means of the membrane translocating sequence.

Xu, et al. have described a method of immunizing guinea pigs with plasmids encoding viral glycoproteins from the Ebola virus. A vaccine delivered by their method has been demonstrated to provide protective immunity, and protection correlated with antibody titer and antigen-specific T-cell responses to the viral glycoproteins. In the method of the present invention, the virion glycoproteins, both secreted form (sGP) and transmembrane form (GP), of Ebola can be produced in a suitable vector, such as *Pichia pastoris*, as a fusion protein with the MTS located either N-terminal or C-terminal to the virion glycoprotein. The purified protein can be delivered by standard means of vaccination for peptide or subunit-based vaccines known to those of skill in the art. The MTS can facilitate entry of the viral glycoprotein into the cell, where antigen processing of the protein can occur. Processed antigen expressed on the cell surface will provide an immune response as has been seen in plasmid-delivery DNA vaccines, without the inherent limitations of plasmid-delivery systems.

An antigen-specific cytotoxic T lymphocyte (CTL) response has been demonstrated by the Naval Medical Research Institute for the circumsporozoite protein of *Plasmodium falciparum* (PfCSP) administered by means of naked plasmid DNA (Wang et al., 1998). The MTS of the present invention and the method of engineering proteins for cell membrane permeability can be used to deliver purified fusion protein comprising the MTS and the PfCSP protein to provide antigenic stimulation of a CTL response. If provided in a suitable carrier, the MTS/PfCSP protein can be produced for oral or aerosol delivery in a more stable form which is appropriate for delivery and administration to subjects at remote locations, without costly and often unavailable measures usually associated with vaccine preservation.

Oral delivery of vaccines using the MTS fusion protein provides a method for delivering antigenic epitopes to the intestinal mucosa, where a strong CTL response can be generated. Alternatively, vaccines can be delivered using deep-lung delivery methods recently developed (Patton, 1997). Most proteins and peptides are absorbed naturally in the lungs, where they pass into the bloodstream. Protein absorption apparently occurs in the alveoli, by a process known as trancytosis. Use of deep-lung delivery methods would provide a non-invasive method of vaccine delivery for fusion proteins produced by the method of the present invention.

Genetically Engineered Proteins With Cell Membrane Permeability for Use in Drug Delivery Systems New protein therapies have been developed for the treatment of previously untreatable conditions, including hepatitis C, hormonal disorders, multiple sclerosis, and some forms of cancer. Protein delivery into the extracellular environment has presented a challenge, because of the large size and fragile three-dimensional structure of proteins. Protein stabilization has been accomplished by techniques as described, for example, in U.S. Pat. No. 5,711,968, (incorporated herein by reference) which describes the use of zinc to stabilize recombinant human growth hormone and recombinant α-interferon in microspheres. U.S. Pat. No. 5,674,534, issued to Zale, et al. (incorporated herein by reference), describes the use of ammonium sulfate to stabilize erythropoietin during release from hydrated microspheres.

Methods of accomplishing sustained delivery of therapeutic protein products have also been described in U.S. Pat. No. 4,767,628, issued to Hutchinson (incorporated herein by reference), and U.S. Pat. No. 4,765,189, issued to Kent, et al. (incorporated herein by reference). Controlled release microspheres, described in U.S. Pat. No. 5,019,400, issued to Gombotz, et al (incorporated herein by reference), and marketed as the ProLease® system (Alkermes, Inc.), provide a powder form of solid protein, homogeneously and rigidly dispersed within porous polymer particles (often made of poly (lactide-co-glycolide), or PLG). An implantable osmotic pump system has also been reported to deliver peptide drugs at a constant rate for up to 1 year (Wright et al., 1997).

The method of genetically engineering proteins with cell membrane permeability described by the present invention provides a means for delivering therapeutic protein products into a cell. Combination of the present invention with previously described methods of extracellular protein delivery provide a method of delivering proteins for import into a cell in a stabilized, functional form in a controlled-release fashion.

Polypeptides are produced using an appropriate expression vector and expression system. Cell membrane permeability is conferred upon the protein or polypeptide by the expression of a fusion protein with the membrane translocating sequence (MTS) located either N-terminal or C-terminal to the expressed polypeptide. Less stable proteins are stabilized by methods known to those of skill in the art and described previously. Delivery to the extracellular environment is accomplished by providing the stabilized fusion protein in an appropriate carrier, such as the microsphere carriers described in U.S. Pat. No. 5,019,400. The protein of choice will dictate the appropriate vector and expression system, as well as the appropriate stabilization and delivery technique. A person of skill in the art of drug delivery systems can choose the appropriate techniques from among those described.

Viral proteins which interfere with antigen presentation by down-regulating MHC class I expression have been identified for viruses such as herpesviruses, adenoviruses, and human immunodeficiency virus (Hengel et al., 1997). Use of these viral proteins to stabilize tissue transplants, such as beta cell transplants for diabetes treatment, against immune attack has been investigated. Gene delivery has been attempted through the use of viral vectors, however, with some success—but with the problems common to viral vector delivery systems. Viral vectors, introducing more protein material than the target protein, carry with them a risk of immune reaction to the vector itself. Particularly where more than one target protein must be delivered to more than one target tissue, these vectors can produce hypersensitivity reactions after repeated delivery. Using the method of the present invention, however, these disadvantages can be overcome. In the case of pancreatic beta cell transplant for diabetes, for example, a time-release drug delivery system can be provided using stabilizing agents such as those described in the references previously mentioned. The target protein for the drug delivery system can be a viral protein that inhibits MHC class I expression on the transplanted cells. This protein can be produced as a fusion protein attached either N-terminal or C-terminal to an MTS as in the present invention. The MTS facilitates delivery of the viral protein to the interior of the cell, where the viral protein inhibits MHC class I expression. In a preferred embodiment of the invention, the viral protein may be the E3 19K protein of human adenovirus.

During et al. demonstrated that lactose intolerance could be treated using peroral application of adeno-associated virus (AAV) encoding the enzyme.

Cancer Therapy Using Cell Permeable Proteins

The method of the present invention provides a means for producing cell-permeable proteins for the treatment of cancer. Regulators of apoptosis and cell cycle control have been found to play a key role in oncogenesis, and gene therapy techniques using intratumoral injection of an adenoviral expression vector encoding the p53 gene have shown promise for the control of some tumors. Delivery of specific protein products through the use of viral vectors has proven to be problematic, however. The MTS and method of the present invention provide a means for producing cell-permeable proteins from among the cell cycle regulators and regulators of apoptosis, as well as other proteins identified to play a role in the development of the cancer state.

For example, in the method of the present invention, the nucleotide sequence encoding the p53 gene can be inserted into a suitable vector, either 5' or 3' to the sequence of an MTS of the present invention. Under expression conditions appropriate for the vector of choice and known to those of skill in the art, a fusion protein comprising an MTS and the p53 protein can be expressed. Attachment of the MTS to the p53 protein renders the p53 protein cell permeable, and protein can be administered to tumor cells to inhibit tumor development. Administration of cell-permeable protein can be accomplished in various ways, including, but not limited to, intratumoral injection, infusion, and intravenous administration. Bax and Bcl-$x_L$ are other examples from among a wide variety of proteins that have been determined to effect cell cycle control and apoptosis, and therefore be effective for cancer therapy. The method of the present invention provides a more efficient, less labor-intensive, less costly method for delivery of anti-oncogenic proteins to tumor cells.

Veterinary Applications of Proteins With Cell Membrane Permeability

A number of canine and feline diseases, as well as bovine and other diseases, provide attractive candidates for protein-based vaccines. Protein-based treatments for cancer and other disorders which have been developed for use in humans also provide therapeutic benefit in veterinary practice. A synthetic peptide vaccine for canine parvovirus (using the amino-terminal region of viral protein VP2), for example, has already proven to protect dogs against subsequent challenge with virulent canine parvovirus (Langeveld et al., 1994).

Proteins With Cell Membrane Permeability Provide a More Effective Method for Vaccine Delivery Using Edible Plants as Vectors Mason, et al. (1998) have described a method of using transgenic plants to provide an edible vaccine against enterotoxigenic *Escherichia coli* by expression of the heat-labile enterotoxin B subunit (LT-B). Agracetus has reported the development of transgenic corn, soybeans, and tobacco for production of recombinant proteins. In the method of the present invention, corn, for example, can be genetically engineered, using recently developed techniques, to produce the fusion protein product of the MTS and the *E. coli* toxin LT-B. Transgenic corn fed to cattle will deliver the fusion protein to the lumen of the intestine, where the MTS will deliver the LT-B antigen to the interior of antigen-processing cells in the intestinal mucosa.

As discussed previously, antigenic proteins have been identified for a number of infectious agents. Methods for producing transgenic plants are known to those of skill in the relevant art, and have been described in the relevant literature. Expression of a synthetic fusion protein in potatoes, for example, under the control of a constitutive promoter provides an accumulation of the fusion protein in the tubers—and a supply of protein antigen for oral administration. Other edible plant species accumulate recombinant protein in leaves, which can be administered in a similar fashion to that previously described for the tubers of raw potatoes.

Antigen concentrations per gram of plant material are readily ascertainable by methods known to those of skill in the relevant art, which include protein isolation by standard means and quantification by standard protein assays. Oral antigen administration of microgram quantities of *E. coli* LT-B antigen, using genetically engineered raw potatoes, has been demonstrated to provide comparable protection in mice to antigen administration by conventional means.

EXAMPLES

Expression of the MTS Fusion Protein

In the present example, glutathione S-transferase from *Schistosoma japonicum* was used as the full-length protein cargo. Two different MTS expression plasmids were constructed, both utilizing the pGEX-3X vector (AMRAD Corporation Limited) which encodes Sj26, the 26-kDa *S. japonicum* glutathione S-transferase (GST). Expression plasmid pGEX-3X-MTS1 and expression plasmid pGEX-3X-MTS2 were constructed so that the MTS coding sequence was located C-terminal to the Sj26 coding region (FIG. 1). Both plasmids contain a factor X cleavage site between GST and the MTS, which allows characterization of the attached MTS following enzyme cleavage. A BamHI restriction endonuclease site located C-terminal to the MTS in pGEX-3X-MTS1 and N-terminal to the MTS in pGEX-3X-MTS2 provides an insertion point for a nucleotide sequence encoding a target polypeptide, protein domain, or full-length protein.

Wild-type GST (GST-WT), GST-MTS1, and GST-MTS2 were expressed in *E. coli* strain DH5α and purified from bacterial cell lysates by glutathione-agarose affinity chromatography. Analysis of the purified GST-MTS1 and GST-MTS2 protein preparations by SDS-PAGE showed predominantly single protein bands (29-kDa) with the predicted increase in apparent molecular size relative to GST-WT (FIG. 2). To confirm the amino acid content of the MTS in GST-MTS proteins, the GST-MTS1 protein was cleaved with factor Xa and the MTS-containing peptide was purified by high performance liquid chromatography (HPLC). The molecular weight (MW) of the purified MTS-containing peptide was determined by mass spectrometry analysis. The molecular weight of the purified MTS peptide matched the predicted value.

Cell Membrane Permeability of the MTS-Protein Fusion Product

Confluent NIH 3T3 cells were incubated with 20 μM of purified GST-MTS1, with GST-WT and untreated cells used as control, in Dulbecco's Modified Eagles Medium (DMEM) for 30 minutes at 37° C. The cells were extensively washed and subsequently analyzed by indirect immunofluorescence assay using anti-GST antibodies. In GST-MTS1 protein-treated cells, strong fluorescent signals were observed in a punctate staining pattern throughout all cells examined (FIG. 3*a*). GST-WT-treated and untreated cells did not display fluorescent signals (FIG. 3*b* and 3*c*). Other cell types were also utilized, including murine endothelial LE-II cells and baby hamster kidney (BHK-21) cells, which exhibited a staining pattern similar to NIH 3T3 cells by the immunofluorescence assay.

Intracellular GST-MTS1 protein was also detected by Western blot analysis of cell lysates using polyclonal anti-GST antibodies. A 29-kDa protein was detected by anti-GST antibodies in cell lysates from cells treated with GST-MTS1 (FIG. 4). GST was not detected in lysates from cells treated with GST-WT.

Flanking sequences of the MTS region did not affect the import activity conferred by the MTS, as GST-MTS2 cellular import was as efficient as that of GST-MTS1.

GST-MTS1 protein was localized intracellularly, as evidenced by confocal laser scanning microscopy. A six-step Z-position 1 μm sectional scanning of the cell exhibited strongest fluorescent signals representing immunoreactive GST-MTS1 protein in the midsections of the cells (FIG. 5).

Influence of Protein Content, Time and Temperature of Incubation on Cellular Import Western blot analysis was used to determine the relative levels of protein imported into the cells. The import of GST-MTS1 protein by NIH 3T3 cells at 37° C. for 30 minutes incubation exhibited dose dependence over a concentration range up to 20 μM (FIG. 6*a*). Higher concentrations have not yet been tested.

Uptake of GST-MTS1 by NIH 3T3 cells occurred equally well at 22° C. and 37° C. (FIG. 6*b*). Protein import was significantly impaired at 4° C., however. At physiological temperatures, imported protein was readily detected after only 30 minutes incubation. Protein import had not reached saturation after 6 hours of incubation. Stability of intracellular GST-MTS1 protein was evidenced by the lack of degradation products after 6 hours incubation.

Imported protein was not localized within cellular compartments such as lysosomes, as evidenced by the observation that GST-MTS1 continued to accumulate intracellularly up to 18 hours incubation with only a low level of degraded protein detected (FIG. 6*c*). Furthermore, intact GST-MTS1 was recovered from lysates of protein-treated cells using glutathione-conjugated agarose beads.

Cells treated with GST-MTS1 at a final extracellular concentration of 20 μM, for 30 minute incubation at 37° C., imported approximately 0.5–$1\times10^6$ molecules of GST-MTS1 protein per cell, as determined by comparison of band intensity in Western blots of the protein recovered from cell lysates to that of known concentrations of the protein.

Lack of Cellular Cytotoxicity of the Protein Import

Protein-treated and untreated cells were stained with fluorescein diacetate-ethidium bromide. After 30 minutes incubation, the percentage of viable cells treated with 20 mM protein was 98.43±0.96, and after 2 hours the percentage of viable protein-treated cells was 98.40±0.95. In protein-untreated cells, viability was 99.43±0.39 and 97.90±0.67, respectively.

Use of Cellular Protein Import to Investigate Intracellular Signaling Processes

Figure 7A:
FIG. 7a and FIG. 7b.
Figure 7B:
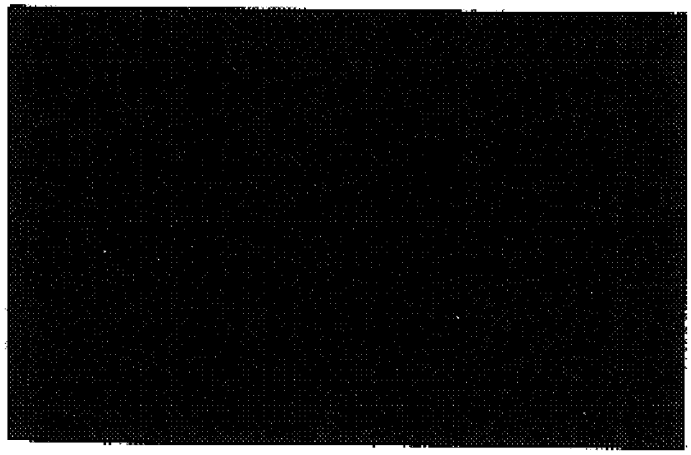
Figure 8A:
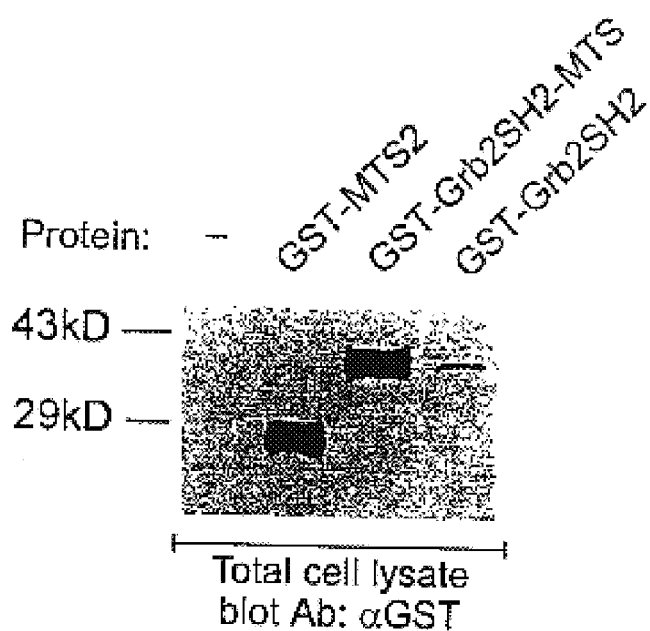
FIG. 8a and FIG. 8b.

A cell-permeable fusion protein containing the Grb2 SH2 domain (which binds to the tyrosine-phosphorylated EGF receptor) was constructed by synthesizing a DNA fragment encoding the human Grb2 SH2 domain (residues 54–164) using the polymerase chain reaction (PCR) and inserting the sequence into GST-MTS2 and pGEX-3X (which contains the glutathione S-transferase coding sequence without the MTS). Protein products from each plasmid construct were expressed in E. coli, and purified. The MTS fusion protein was efficiently transported into SAA cells, as determined by indirect immunofluorescence spectroscopy (FIG. 7a and 7b) and Western blot analysis (FIG. 8a).

Figure 8B:
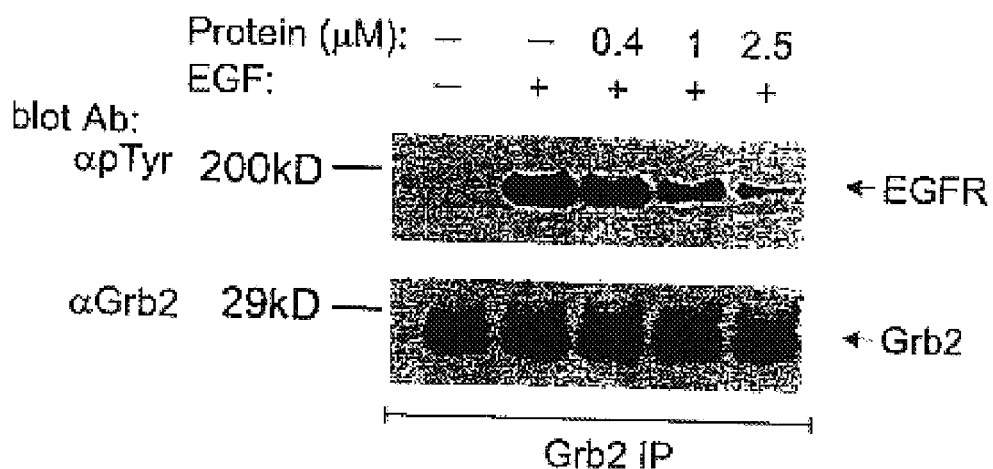
Figure 9:
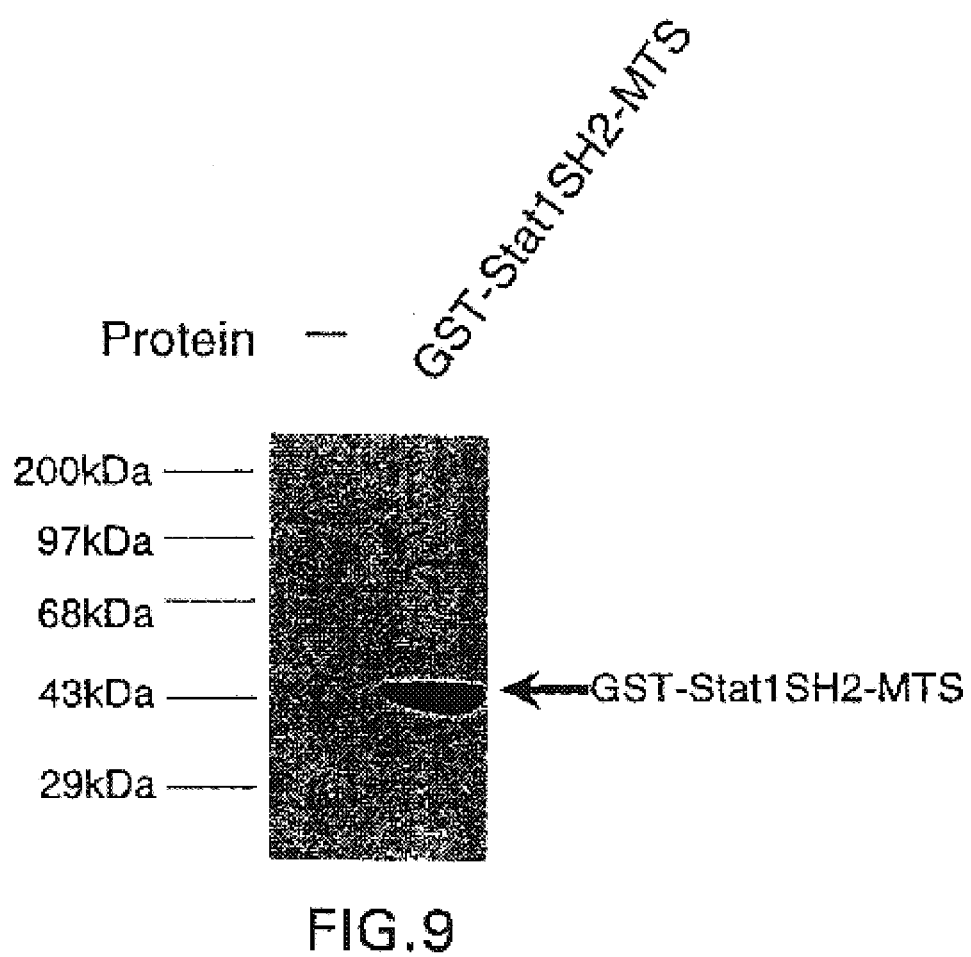
FIG. 9 illustrates Western blot analysis, using anti-GST antibody, of the intracellular level of GST-Stat1SH2 imported into the cell as a GST-Stat1SH2-MTS fusion product. Lysates of untreated cells were run in the lane marked "-", and lysates of cells treated with the GST-Stat1 SH2-MTS fusion product were run in the lane marked "GST-Stat1SH2-MTS." The GST-Stat1SH2-MTS product migrated to the predicted 43 kDa location, demonstrating that a protein of this size could be imported into the cell when fused to the MTS.

Serum-starved SAA cells (NIH 3T3 cells overexpressing epidermal growth factor receptor) were incubated with GST-Grb2SH2-MTS protein or control proteins for 1 hour prior to epidermal growth factor stimulation. Phosphorylated EGFR associated with endogenous Grb2 was examined in coimmunoprecipitation assays. Probes were specific for phosphorylated EGF receptor and Grb2 protein. Inducible EGFR/Grb2 association was inhibited in cells pretreated with GST-Grb2SH2-MTS. No significant inhibition was observed in cells pretreated with the non-cell permeable GST-Grb2SH2 protein or nonfunctional GST-MTS2 protein. Inhibition of EGFR/Grb2 association by GST-Grb2SH2-MTS was dose-dependent (FIG. 8b), reaching 35% at 0.4 $\mu$M, 62% at 1 $\mu$M, and 93% at 2.5 $\mu$M final extracellular concentration as determined by densitometric analysis.

Pretreatment of cells with GST-Grb2SH2-MTS protein substantially inhibited the EGFR-induced MAP kinase activation involved in downstream mitogenic signaling. Specificity of binding of EGFR to GST-Grb2SH2-MTS was confirmed by coimmunoprecipitation assay with anti-GST antibodies.

The following references, to the extent that they provide details supplementary to those set forth herein, are specifically incorporated herein by reference:

Chen, et al. (1998), "Protective Immunity Induced by Oral Immunization with a Rotavirus DNA Vaccine Encapsulated in Microparticles," J. Virol. 72(7): 5757–5761.

Chinsangaram, et al. (1998), "Antibody Response in Mice Inoculated with DNA Expressing Foot-and-Mouth Disease Virus Capsid Proteins," J. Virol. 72(5): 4454–4457.

Derossi et al. (1994), "The Third Helix of the Antennapedia Homeodomain Translocates Through Biological Membranes," J. Biol. Chem. 269(14): 10444–10450.

Dokka, et al. (1997), "Cellular Delivery of Oligonucleotides by Synthetic Import Peptide Carrier," Pharmaceutical Research 14: 1759–1764.

Griffin, et al. (1998), "Specific Covalent Labeling of Recombinant Protein Molecules Inside Living Cells," Science 281:269–272.

Hengel, H. et al. (1997), "Interference with Antigen Processing by Viruses," Curr. Opin. Immunol. 9(4): 470–6.

Jones et al. (1998), "Role of Dynamin in the Formation of Transport Vesicles from the Trans-Golgi Network," Science 279: 573–577.

King, et al., (1981), "Biochemical Identification of Viruses Causing the 1981 Outbreaks of Foot-and-Mouth Disease in the UK," Nature 293: 479–480.

Kohler, et al., (1997), "Exchange of Protein Molecules Through Connections Between Higher Plant Plastids," Science 276: 2039–2042.

Langeveld, et al., (1994), "First Peptide Vaccine Providing Protection Against Viral Infection in the Target Animal: Studies of Canine Parvovirus in Dogs," J. Virol. 68(7): 4506–4513.

Lewin, Benjamin (1994), Genes V, Oxford University Press, p. 290.

Lin et al., (1995), J. Biol. Chem. 270(24): 14255–14258.

Mason, et al. (1998), "Edible Vaccine Protects Mice Against Escherichia coli Heat-Labile Enterotoxin (LT): Potatoes Expressing a Synthetic LT-B Gene," Vaccine 16(13): 1336–1343.

Mathews, et al., (1992), "A Synthetic Peptide to the E Glycoprotein of Murray Valley Encephalitis Virus Defines Multiple Virus-Reactive T- and B-cell Epitopes," J. Virol. 66(11): 6555–6562.

No, et al., (1996), "Ecdysone-inducible Gene Expression in Mammalian Cells and Transgenic Mice,"'Proc. Natl. Acad. Sci USA 93: 3346–3351.

Olson, et al., (1995), "Analysis of MAP4 Function in Living Cells Using Green Fluorescent Protein (GFP) Chimeras," J. Cell. Biol. 130(3): 639–650.

Patton, J. (1997), "Deep-lung Delivery of Therapeutic Proteins," CHEMTECH 27(12): 34–38.

Tam, et al., "Peptide Synthesis Using Unprotected Peptides Through Orthogonal Coupling Methods," Proc. Natl. Acad. Sci. USA 92: 12485–12489.

Tsien, R. Y. (1998), Annu. Rev. Biochem, 67: 509.

Wang, et al (1998), "Induction of Antigen-Specific Cytotoxic T Lymphocytes in Humans by a Malaria DNA Vaccine," Science 282: 476–480.

Wright, et al. (1997), Proc. Int. Symp. Controlled Release Bioact. Mater. 24: 59.

Xu, et al. (1998), "Immunization for Ebola Virus Infection," Nat. Med. 4(1): 37–42.

What is claimed is:

1. An isolated peptide of about eight to about fifty residues, wherein the isolated peptide comprises at least eight consecutive residue of SEQ ID NO: 1 (Ala-Ala-Val-Leu-Leu-Pro-Val-Leu-Leu-Ala-Ala-Pro.

2. The isolated peptide of claim 1, wherein the isolated peptide comprises at least nine consecutive residues of SEQ ID NO: 1.

3. The isolated peptide of claim 1, wherein the isolated peptide comprises at least ten consecutive residues of SEQ ID NO: 1.

4. The isolated peptide of claim 1, wherein the isolated peptide comprises at least eleven consecutive residues of SEQ ID NO: 1.

5. The isolated peptide of claim 1, wherein the isolated peptide comprises SEQ ID NO: 1.

* * * * *

UNITED STATES PATENT AND TRADEMARK OFFICE
CERTIFICATE OF CORRECTION

PATENT NO. : 6,780,843 B2
DATED : August 24, 2004
INVENTOR(S) : Lin et al.

It is certified that error appears in the above-identified patent and that said Letters Patent is hereby corrected as shown below:

Column 35,
Line 52, after "1." and before "isolated" please delete "Art" and substitute -- An --.
Line 52, after "to" please delete "shout" and substitute -- about --.
Line 54, after "consecutive" please delete "residue" and substitute -- residues --.
Line 55, after "Ala-Pro", and before the period ".", insert the right parenthesis -- ) --.

Signed and Sealed this

Twenty-eighth Day of June, 2005

JON W. DUDAS
*Director of the United States Patent and Trademark Office*